US010391163B2

(12) United States Patent
Liang et al.

(10) Patent No.: US 10,391,163 B2
(45) Date of Patent: Aug. 27, 2019

(54) BIRD FLU VACCINE COMBINATION COMPRISING VIRUS-LIKE PARTICLES AND NOVEL ADJUVANTS

(71) Applicant: Academia Sinica, Taipei (TW)

(72) Inventors: Shu-Mei Liang, Taipei (TW); Pei-Wen Hsiao, Taipei (TW); Ming-Chu Cheng, Taipei (TW); Yu-Chih Yang, New Taipei (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 15/756,774

(22) PCT Filed: Sep. 9, 2016

(86) PCT No.: PCT/US2016/051160
§ 371 (c)(1),
(2) Date: Mar. 1, 2018

(87) PCT Pub. No.: WO2017/044890
PCT Pub. Date: Mar. 16, 2017

(65) Prior Publication Data
US 2018/0243402 A1  Aug. 30, 2018

Related U.S. Application Data

(60) Provisional application No. 62/216,865, filed on Sep. 10, 2015.

(51) Int. Cl.
*A61K 39/145* (2006.01)
*C12N 7/00* (2006.01)
*A61K 39/12* (2006.01)
*A61K 39/135* (2006.01)
*A61K 39/00* (2006.01)
*A61P 31/16* (2006.01)

(52) U.S. Cl.
CPC ............ *A61K 39/145* (2013.01); *A61K 39/12* (2013.01); *A61K 39/135* (2013.01); *C12N 7/00* (2013.01); *A61K 2039/5258* (2013.01); *A61K 2039/552* (2013.01); *A61K 2039/555* (2013.01); *A61K 2039/55505* (2013.01); *A61K 2039/55511* (2013.01); *A61K 2039/572* (2013.01); *A61K 2039/70* (2013.01); *A61P 31/16* (2018.01); *C12N 2760/16123* (2013.01); *C12N 2760/16134* (2013.01); *C12N 2760/16151* (2013.01); *C12N 2770/00034* (2013.01); *C12N 2770/32122* (2013.01); *C12N 2770/32123* (2013.01)

(58) Field of Classification Search
None
See application file for complete search history.

(56) References Cited

U.S. PATENT DOCUMENTS

| 7,763,450 B2 * | 7/2010 | Robinson | A61K 39/145 435/235.1 |
| 2014/0271697 A1 * | 9/2014 | Massare | C07K 14/005 424/186.1 |
| 2016/0220659 A1 | 8/2016 | Audonnet et al. | |

OTHER PUBLICATIONS

International Search Report for PCT/US2016/051160, dated Feb. 12, 2016.
Written Opinion of International Search Authority for PCT/US2016/051160, dated Feb. 12, 2016.

* cited by examiner

*Primary Examiner* — Shanon A. Foley
*Assistant Examiner* — Myron G Hill
(74) *Attorney, Agent, or Firm* — Hsiu-Ming Saunders; Intellectual Property Connections, Inc.

(57) ABSTRACT

A vaccine composition is disclosed. The vaccine composition comprises: (a) a therapeutically effective amount of an influenza virus-like particle (VLP) comprising: (i) influenza M1, influenza M2, influenza hemagglutinin (HA), and influenza neuraminidase (NA) proteins; (b) Foot-and-mouth disease virus (FMDV) capsid protein VP3, recombinant FMDV VP3 (rVP3), VP3 peptide, or SUMO VP3; and (c) alum. Also disclosed is use of a vaccine composition according to the invention in the manufacture of a medicament for inducing an immunogenic response in a subject in need thereof.

19 Claims, 3 Drawing Sheets

Specification includes a Sequence Listing.

| Chicken group | VLP stimulation | | Chicken group | Inactivated virus stimulation | |
|---|---|---|---|---|---|
| | INF-γ | IL-18 | | INF-γ | IL-18 |
| PBS | 1 | 1 | PBS | 1 | 1 |
| VLP+VP3+Alum | 4.6 | 2.2 | Inactivated Virus+VP3+Alum | 2.5 | 1.1 |

BIRD FLU VACCINE COMBINATION COMPRISING VIRUS-LIKE PARTICLES AND NOVEL ADJUVANTS

REFERENCE TO RELATED APPLICATION

This application is a national stage application (under 35 U.S.C. 371) of PCT/US2016/051160 filed on 9 Sep. 2016, which claims priority to U.S. provisional application 62/216,865 filed on 10 Sep. 2015, all of which are herein incorporated by reference in their entireties.

FIELD OF THE INVENTION

The present invention relates generally to vaccines, more specifically to bird flu vaccines.

BACKGROUND OF THE INVENTION

Avian flu is a major disease in poultry. The disease is caused by avian influenza virus (AIV). Highly pathogenic avian influenza such as H5N1 and H5N2 strain resulted in the deaths of hundreds of millions of birds, including poultry. Current commercial vaccine against the highly pathogenic avian influenza virus (HPAIV) is made from inactivated viruses. This vaccine may not be as effective against a newly mutated highly pathogenic strain. Furthermore, birds vaccinated with inactivated virus vaccine cannot be distinguished from infected birds, which can cause great difficulty to monitor the epidemics. Therefore, development of new and effective vaccine against AIV to control the spread of HPAIV is needed. For these concerns, subunit vaccine is a preferred design over the whole viral vaccine. Virus-like particle (VLP) which represents the structure and antigen compositions of whole virus is a potent vaccine antigen and lacks the risks of growing virus.

SUMMARY OF THE INVENTION

In one aspect, the invention relates to a vaccine composition comprising:
  (a) a therapeutically effective amount of an influenza virus-like particle (VLP) comprising:
    (i) influenza M1, influenza M2, influenza hemagglutinin (HA), and influenza neuraminidase (NA) proteins;
  (b) a recombinant capsid VP3 protein (rVP3) of foot-and-mouth disease virus; and
  (c) alum.

In another aspect, the invention relates to a vaccine composition comprising:
  (a) a therapeutically effective amount of an influenza virus-like particle (VLP) comprising:
    (i) influenza M1, influenza M2, influenza hemagglutinin (HA), and influenza neuraminidase (NA) proteins;
  (b) Foot-and-mouth disease virus (FMDV) capsid protein VP3, recombinant FMDV VP3 (rVP3), VP3 peptide, or SUMO VP3; and
  (c) alum.

In one embodiment of the invention, the influenza HA and NA proteins are avian influenza HA and NA proteins.

In another embodiment, the avian influenza HA and NA proteins are selected from the group consisting of H5N2, H5N1 and H5N8.

In another aspect, the invention relates to a method of formulating a vaccine composition of the invention, in which the method comprises adding the therapeutically effective amount of the influenza VLP to the VP3, rVP3, VP3 peptide, or SUMO VP3 and alum.

Further in another aspect, the invention relates to use of a vaccine composition of the invention in the manufacture of a medicament for inducing an immunogenic response in a subject in need thereof.

The invention also relates to a vaccine composition of the invention for use in inducing an immunogenic response in a subject in need thereof. Alternatively, the invention relates to a method for inducing an immunogenic response in a subject in need thereof, comprising administering to the subject in need thereof a vaccine composition of the invention to induce an immunogenic response.

The subject may be at least one selected from the group consisting of mammalian and avian animals.

Further in another aspect, the invention relates to an influenza virus-like particle (VLP) comprising influenza M1, influenza M2, influenza hemagglutinin (HA), and influenza neuraminidase (NA) proteins.

Alternatively, the invention relates to an influenza virus-like particle (VLP) comprising:
  (a) an influenza virus M1 core protein that can self assemble into a VLP core; and
  (b) influenza HA and NA proteins expressed on the surface of the VLP;
  wherein the VLP is non-replicative and noninfectious and does not contain intact viral nucleic acids. The influenza VLP may further comprise influenza M2 protein expressed on the surface of the influenza VLP.

Further in another aspect, the invention relates to a host cell comprising an influenza VLP of the invention.

In one embodiment, the host cell is a Vero cell or 293T cell.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

DETAILED DESCRIPTION OF THE INVENTION

The present invention is more particularly described in the following examples that are intended as illustrative only since numerous modifications and variations therein will be apparent to those skilled in the art. Various embodiments of the invention are now described in detail. Referring to the drawings, like numbers indicate like components throughout the views. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise. Moreover, titles or subtitles may be used in the specification for the convenience of a reader, which shall have no influence on the scope of the present invention. Additionally, some terms used in this specification are more specifically defined below.

Definitions

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

VP3 is one of the capsid proteins of FMDV. Four structural proteins, VP1, VP2, VP3 and VP4, comprise the viral capsid of the FMDV.

rVP3 is a recombinant DNA derived VP3-like protein expressed and purified from E. coli. A T7 tag and a His tag were attached to the N-terminus and the C-terminus of the VP3 protein, respectively.

VP3 peptide is a polypeptide consisting of FMDV VP3 residues 91-150.

SUMO VP3 is a VP3 fusion protein in which VP3 is fused to a hexahistidine-tagged yeast SUMO (small ubiquitin-related modifier) protein.

Development of new and effective vaccines to protect humans and animals from influenza virus infection and to control the spread of influenza viruses is an important quest worldwide. Both antigen preparation and adjuvant are important components of vaccine. Virus-like particle (VLP) which represents the structure and antigen compositions of whole virus is a potent vaccine antigen and lacks the risks of growing virus. We found the combination of VLP and rVP3 and alum as vaccines against bird flu yielded the best protection. Chicken immunized with H5N2-VLP adjuvant with rVP3 and alum protected 100% of chicken from H5N2 virus challenge resulting in less virus shedding than chicken immunized with inactivated virus adjuvant with rVP3 and alum. Our data suggest that VLP adjuvant with rVP3 and alum as novel vaccines against flu.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

VP3 and VLP were prepared according to the U.S. Pat. Nos. 8,980,281 and 8,795,678, which are enclosed herein by reference in their entireties.

FMDV VP3 protein was expressed and purified from E. coli. Briefly, the gene encoding FMDV VP3 was cloned into a pET-24a (Novagen, Madison, Wis., USA) expression vector and transformed into BL21-CodonPlus (DE3)-RIL strain (Stratagene, Calif., USA). The E. coli expressing recombinant VP3 was broken up with a microfluidizer (M-110Y Cell Disruption) in TEN buffer (20 mM Tris-HCl, pH 8.0, 1 mM EDTA, 100 mM NaCl). The bacterial lysate was centrifuged, and the pellet was sequentially washed with 0.05% deoxycholate in TEN buffer, 25% sucrose in TEN buffer and TEN buffer alone. The pellet was finally solubilized by binding buffer (20 mM Tris-HCl, 100 mM NaCl, 8 M urea) and the VP3 was purified by cobalt affinity column with a step gradient of imidazole. The fractions containing VP3 proteins were pooled together and then diluted in a drop-wise fashion with 10X volume of refolding buffer (20 mM Tris, 5 µM β-Mercaptoethanol) and incubated at 4° C. for 1 h. The refolded VP3 was dialyzed against 10× volume of dialysis buffer (20 mM Tris, 100 mM NaCl, 2 µM β-Mercaptoethanol) at 4° C. overnight.

```
rVP3 protein sequence (SEQ ID NO: 1),
241 amino acids:
MASMTGGQQMGRGSGIFPVACSDGYGGLVTTDPKTADPVYGKVFNPPRNL

LPGRFTNLLDVAEACPTFLHFDGDVPYVTTKTDSDRVLAQFDLSLAAKHM

SNTFLAGLAQYYTQYSGTINLHFMFTGPTDAKARYMVAYAPPGMEPPKTP

EAAAHCIHAEWDTGLNSKFTFSIPYLSAADYAYTASDBAETTMBQGWGCL

FQITHGKADGDALVVLASAGKDFDLRLPVDARTQLEHHHHH

VP3 protein sequence (SEQ ID NO: 2),
220 amino acids:
GIFPVACSDGYGGLVTTDPKTADPVYGKVFNPPRNLLPGRFTNLLDVAEA

CPTFLHFDGDVPYVTTKTDSDRVLAQFDLSLAAKHMSNTFLAGLAQYYTQ
```

-continued

YSGTINLHFMFTGPTDAKARYMVAYAPPGMEPPKTPEAAAHCIHAEWDTG

LNSKFTFSIPYLSAADYAYTASDBAETTMVQGWBCLFQITHGKADGDALV

VLASAGKDFDLRLPVDARTQ

VP3 peptide sequence (SEQ ID NO: 3),
60 amino acids:
LAGLAQYYTQYSGTINLHFMFTGPTDAKARYMVAYAPPGMEPPKTPEAAA

HCIHAEWDTG

SUMO VP3 protein sequence (SEQ ID NO: 4),
330 amino acids:
HHHHHHMSDSEVNQEAKPEVKPEVKPETHINLKVSDGSSEIFFKIKKTTP

LRRLMEAFAKRQGKEMDSLRFLYDGIRIQADQTPEDLKMEDNDIIEAHRE

QIGGATYGGMGIFPVACSDGYGGLVTTDPKTADPVYGKVFNPPRNLLPGR

FTNLLDVAEACPTFLHFDGDVPYVTTKTDSDRVLAQFDLSLAAKHMSNTF

LAGLAQYYTQYSGTINLHFMFTGPTDAKARYMVAYAPPGMEPPKTPEAAA

HCIHAEWDTGLNSKFTFSIPYLSAADYAYTASDBAETTMVQGWBCLFQIT

HGKADGDALVVLASAGKDFDLRLPVDARTQ

M1 sequence (SEQ ID NO: 5), 252 amino acids
MSLLTEVETYVLSIVPSGPLKAEIAQRLEDVFAGKNTDLEALMEWLKTRP

ILSPLTKGILGFVFTLTVPSERGLQRRRFVQNALNGNGDPNNMDKAVKLY

RKLKREITFHGAKEIALSYSAGALASCMGLIYNRMGAVTTEVAFGLVCAT

CEQIADSQHRSHRQMVATTNPLIRHENRMVLASTTAKAMEQMAGSSEQAA

EAMEIASQARQMVQAMRAIGTHPSSSTGLRDDLLENLQTYQKRMQVQMQR

FK

M2 sequence (SEQ ID NO: 6), 97 amino acids
MSLLTEVETPIRNEWGCRCNDSSDPLVVAANIIGILHLILWILDRLFFKC

VYRLFKHGLKRGPSTEGVPESMREEYRKEQQNAVDADDSHFVSIELE

H5 sequence (SEQ ID NO: 7), 564 amino acids
MERIVIAFAIVNIVTGDRICIGYHANNSTTQVDTIMEKNVTVTHAQDILE

KEHNGRLCSLKGVKPLLILKNCSVAGWLLGNPMCDEFLNAPEWSYIVEKD

RPSNGLCYPGTFNYYEELKHLMSSTNQFEKIQIFPRSSWSNHDASSGVSS

ACPYNGRSSFFRNVVWLIKKNNVYRTITRTYNNTNIEDLLIIWGIHHPNN

AAEQIKLYQNPSTYVSVGTSTLNQRSIPEIATRPKVNGQSGRMEFFWTIL

RPNDSITFESTGNFIAPEYAYKIVKKGDSAIMKSELSYSNCDTKCQTPVG

AINSSMPFHNVHPFAIGECPKYVKLKKLVLATGLRNIPQRRKRGLFGAIA

GFIEGGWQGMVDGWYGYHHSNEQGSGYAADKESTQKAVDGITNKVNSIIS

KMNSQFEAVGKEFNNLERRIENLNKKMEDGFIDVWTYNAELLVLMENERT

LDLHDSNVKNLYDKVRRQLRDNAKELGNGCFEYHRCDNKCMESVRNGTYD

YPQYSEESRLKREEIDGVKLESMGVYQIISIYSTVASSLALAIMVAGLSF

WMCSNGSLQCRVCI

N2 sequence (SEQ ID NO: 8), 449 amino acids
MNPNQKIITIGSVSLTIATVCFLMQIAILTMTVTLHFNQNECSIPANNQV

VPCEPIIEKSINYRDWSKPQCRITGFAPFSKDNSIRLSAGGNIWVTREPY

VSCDTSKCYQFALGQGTTLDNKHSNGTIHDRPTHRTLLMSELGVPFHLGT

KQVCIAWSSSSCHDGKAWLHVCVTGDDKNATASFIYDGMLVDSIGSWSQN

ILRTQESECVCINGTCTVVMTDGSASGKADTRILFIEEGQVIHISPLSGS

AQHIEECSCYPRYPNVRCVCRDNWKGSNRPVVDINMADYSIDSSYVCSGL

VGDTPRNDDSSSSNCRDPNNEKGNPGVKGWAFDDGDDIWMGRTISKDSR

SGYETFRVIDGWTIANSKSQINRQVIVDNNNWSGYSGIFSVENKSCINRC

FYVELIRGRPKETRVWWTSNSIVAFCGTSGTYGTGSWPDGANINFMPI

Example 1

Expression and Purification of Influenza VLPs from Vero Cells. Establishment of Vero Cell System Producing Influenza VLPs is according to U.S. Pat. No. 8,980,281.

Figure 1:
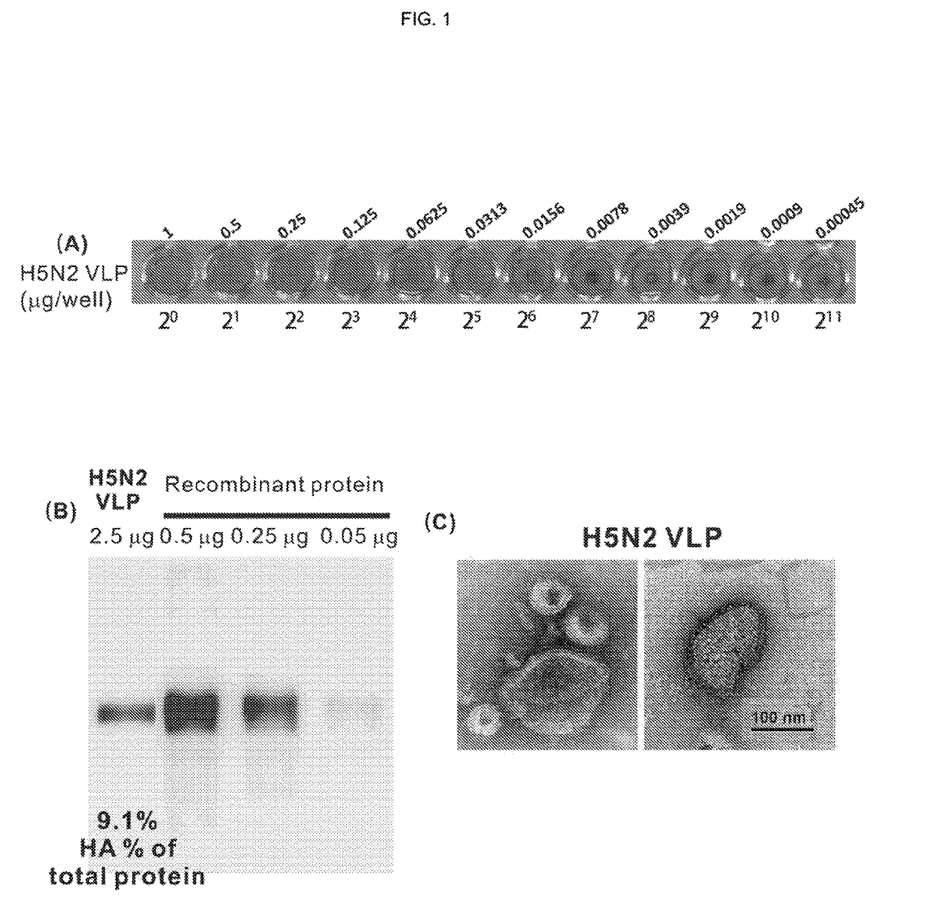
FIG. 1 shows characterization of H5N2-VLP produced by Vero E6 cell. (A) The titer of hemagglutination. (B) Quantification of HA proteins by western blotting. (C) Morphology of H5N2-VLP observed by transmission electron microscope.

Based on an established platform disclosed in U.S. Pat. No. 8,980,281, we successfully created H5N2-VLP producer cell line clones by sequential stable transfection of pCI6/TO-M1-M2 and pCI4/TO-HA-NA plasmids into 293T cells. We also used Vero E6 cells to generate influenza H5N2-VLPs in Vero cells. In brief, we constructed a plasmid harboring two expression cassettes to allow tetracycline-inducible expression of H5 and N2 of avian influenza virus. By stable transfection of the expression plasmid in the founder cell line followed by clone isolation, we screened and identified a producer cell line for H5N2-VLP. Expression and secretion of the VLP from the producer cells was performed in microcarrier suspension culture system with ensuing doxycycline induction. After centrifugation purification of conditioned media, the particle morphologies (FIG. 1C), average sizes, and hemagglutination abilities of secreted VLPs were characterized, and the VLP constituents were quantified by total protein amount. We found that the Vero cells in this manner were better VLP producers than 293T cells. They contained higher abundance of hemagglutinin (HA) protein and as much as 9% of total VLP protein (FIGS. 1A and B). Moreover, the titer of hemagglutination in VLP produced by Vero E6 cell was 4 folds higher than that produced by 293T cell. Therefore, H5N2-VLP produced in Vero E6 cells were used as antigen for bird flu vaccine.

Figure 2:
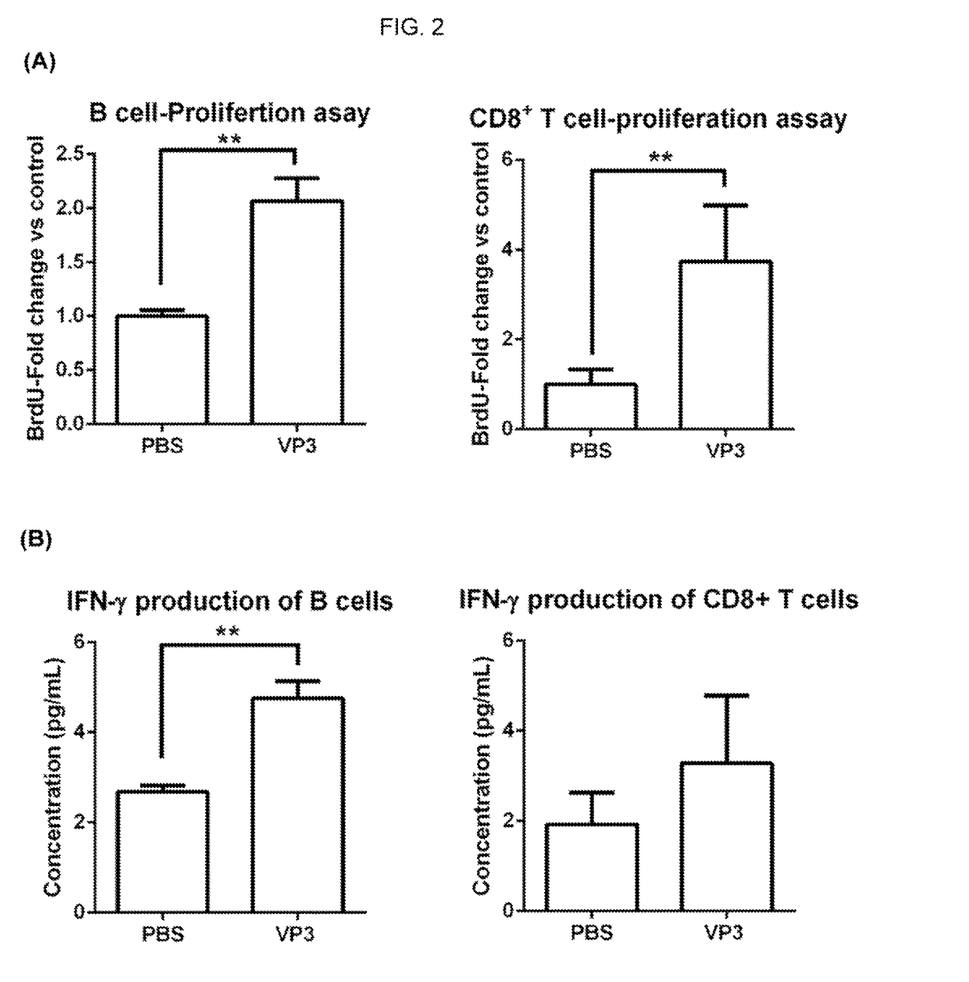
FIG. 2 shows that rVP3 protein significantly stimulates the proliferation of chicken B cells (A, left panel) and CD8+ T cells (A, right panel) and induces chicken immune cells to produce IFN-γ (B).

Both antigen preparation and adjuvant are important components of vaccine. To search for better adjuvants, we cloned VP3 gene of capsid protein of foot and mouth virus. The plasmid containing VP3 gene was over-expressed in *E. coli*, purified and refolded to have adjuvant activity. We then investigated whether rVP3 could activate immune responses in chicken immune cells. We found that rVP3 stimulated the proliferation of chicken B cells and CD8+ T cells (FIG. 2A). rVP3 also induced these chicken immune cells to produce IFN-γ (FIG. 2B). These results indicated that rVP3 induces cellular immune responses of chicken immune cells in vitro.

Figure 3:
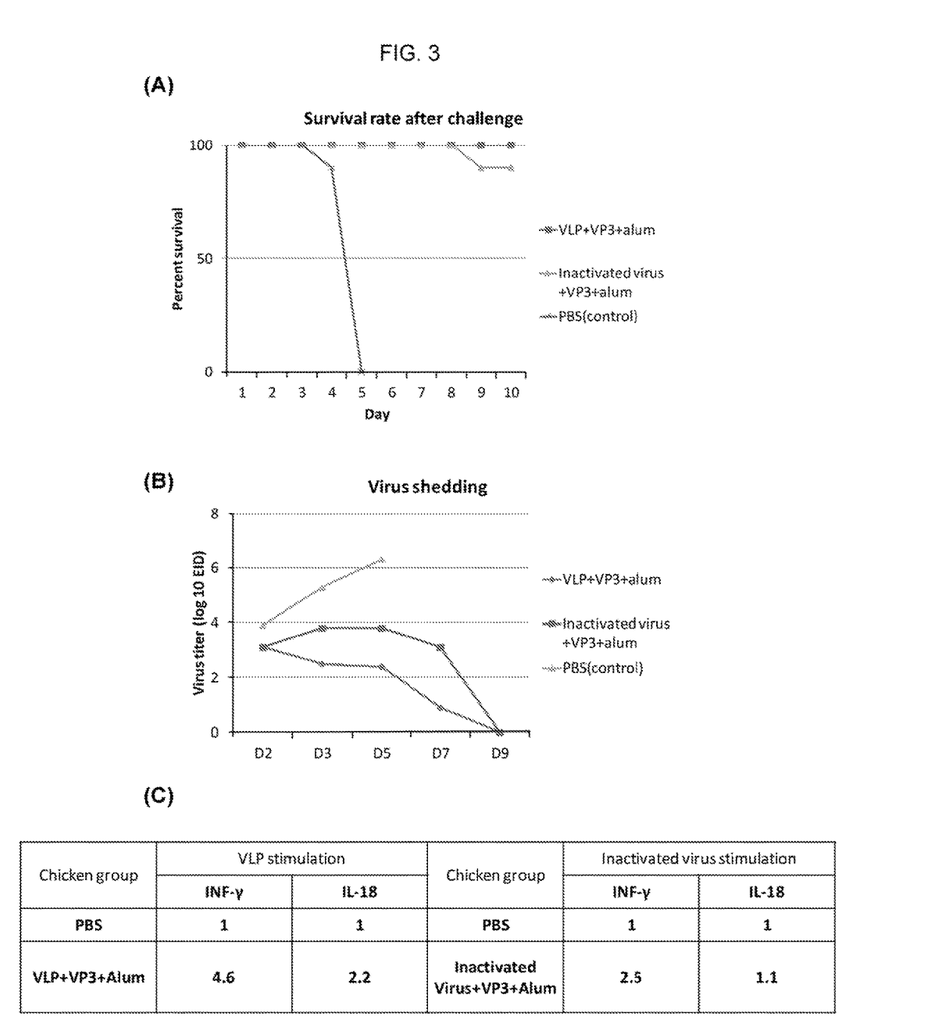
FIG. 3 shows that after being immunized with VLP (with rVP3 and alum as adjuvants), chicken elicit a higher amount of IFN-γ (B), survive fully from a virus challenge (A) and shed less virus than those immunized with inactivated virus (C).

To examine the vaccine efficacy of H5N2-VLP and rVP3, we first immunized chicken with H5N2-VLP alone and found that it did not elicit sufficient antibody titers suggesting that H5N2-VLP required assistance of adjuvant(s) to induce full immune responses. Chicken immunized with low dose of H5N2-VLP adjuvanted with alum were sicker 10 days after challenge than chicken immunized with same dose of H5N2-VLP adjuvanted with rVP3 and alum or same dose of inactivated virus with alum. Chicken primed and boosted with higher dose of H5N2-VLP adjuvant with rVP3 and alum elicited higher hemagglutination inhibition (HI) and serum neutralization (SN) titers similar to that of inactivated virus adjuvant with rVP3 and alum. In addition, chicken immunized with H5N2-VLP adjuvant with rVP3 and alum fully survived from H5N2 virus challenge (FIG. 3A), yielded less virus shedding that were even better than inactivated virus vaccine adjuvant with rVP3 and alum (FIG. 3B). In consistent with our chicken immune cell in vitro study, chicken immunized with H5N2-VLP adjuvant with rVP3 and alum induced IFN-γ and IL18 production higher than that induced by inactivated virus adjuvant with rVP3 and alum (FIG. 3C).

Example 2

Using the similar method as described above, we generate H5N1-VLP producer cell line clones by sequential stable transfection of pCI6/TO-M1-M2 and pCI4/TO-HA-NA plasmids into 293T cells. We also used Vero E6 cells to generate influenza H5N1-VLPs in Vero cells. In brief, we constructed a plasmid harboring two expression cassettes to allow tetracycline-inducible expression of H5 and N1 of avian influenza virus. By stable transfection of the expression plasmid in the founder cell line followed by clone isolation, we screened and identified a producer cell line for H5N1-VLP. Expression and secretion of the VLP from the producer cells was performed in microcarrier suspension culture system with ensuing doxycycline induction. After centrifugation purification of conditioned media, the particle morphologies, average sizes, and hemagglutination abilities of secreted VLPs are characterized, and the VLP constituents are quantified by total protein amount. H5N1-VLP produced in Vero E6 cells are used as antigen for bird flu vaccine.

Example 3

Using the similar method as described above, we generate H5N8-VLP producer cell line clones by sequential stable transfection of pCI6/TO-M1-M2 and pCI4/TO-HA-NA plasmids into 293T cells. We also used Vero E6 cells to generate influenza H5N8-VLPs in Vero cells. In brief, we constructed a plasmid harboring two expression cassettes to allow tetracycline-inducible expression of H5 and N8 of avian influenza virus. By stable transfection of the expression plasmid in the founder cell line followed by clone isolation, we screened and identified a producer cell line for H5N8-VLP. Expression and secretion of the VLP from the producer cells was performed in microcarrier suspension culture system with ensuing doxycycline induction. After centrifugation purification of conditioned media, the particle morphologies, average sizes, and hemagglutination abilities of secreted VLPs are characterized, and the VLP constituents are quantified by total protein amount. H5N8-VLP produced in Vero E6 cells are used as antigen for bird flu vaccine.

In conclusion, we have discovered a new vaccine against high pathogenic avian influenza virus. This new avian flu vaccine consists of avian flu VLPs as antigen and rVP3 and alum as adjuvants. This vaccine can induce high titers of neutralizing antibodies and cell mediated immunity in immunized chicken. It protects chicken against high pathogenic avian virus challenge with less virus shedding. This vaccine may be used as a vaccine against avian flu virus to protect poultry industry, poultry egg industry and human from the outbreak of avian flu virus epidemic.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

What is claimed is:

1. An adjuvanted influenza vaccine composition with adjuvants, comprising:
   (a) an influenza virus-like particle (VLP) a therapeutically effective amount against influenza infection, comprising:
      (i) influenza M1, influenza M2, influenza hemagglutinin (HA), and influenza neuraminidase (NA) proteins; and
   (b) the adjuvants, comprising:
      (1) a recombinant capsid VP3 protein (rVP3) of foot-and-mouth disease virus; and
      (2) alum.

2. An adjuvanted influenza vaccine composition with adjuvants, comprising:
   (a) an influenza virus-like particle (VLP) in a therapeutically effective amount against influenza infection, comprising:
      (i) influenza M1, influenza M2, influenza hemagglutinin (HA), and influenza neuraminidase (NA) proteins;
   (b) the adjuvants, comprising:
      (1)Foot-and-mouth disease virus (FMDV) capsid protein VP3, recombinant FMDV VP3 (rVP3), VP3 peptide, or SUMO VP3; and
      (2) alum.

3. The adjuvanted influenza vaccine composition of claim 1, wherein the influenza HA and NA proteins are avian influenza HA and NA proteins.

4. The adjuvanted influenza vaccine composition of claim 3, wherein the avian influenza HA and NA proteins are selected from the group consisting of H5N2, H5N1 and H5N8.

5. A method for vaccination against influenza infection in a subject in need thereof, comprising:
   administering to the subject in need thereof the adjuvanted influenza vaccine composition of claim 1.

6. The method of claim 5, wherein the subject is at least one selected from the group consisting of humans and birds.

7. A method for vaccination against avian influenza infection in a subject in need thereof, comprising:
   administering to the subject in need thereof the adjuvanted influenza vaccine composition of claim 3.

8. The method of claim 7, wherein the subject is avian.

9. A method for vaccination against avian influenza infection in a subject in need thereof comprising:
   administering to the subject in need thereof the adjuvanted influenza vaccine composition of claim 4.

10. The adjuvanted influenza vaccine composition of claim 2, wherein the influenza HA and NA proteins are avian influenza HA and NA proteins.

11. A method for vaccination against influenza infection in a subject in need thereof, comprising:
    administering to the subject in need thereof the adjuvanted influenza vaccine composition of claim 2.

12. The adjuvanted influenza vaccine composition of claim 10, wherein the avian influenza HA and NA proteins are selected from the group consisting of H5N2, H5N1 and H5N8.

13. A method for vaccination against avian influenza infection in a subject in need thereof, comprising:
    administering to the subject in need thereof the adjuvanted influenza vaccine composition of claim 12.

14. The method of claim 13, wherein the subject is at least one selected from the group consisting of humans and birds.

15. The method of claim 13, wherein the subject is a chicken.

16. The method of claim 4, wherein the subject is at least one selected from the group consisting of humans and birds.

17. The method of claim 4. wherein the subject is a chicken.

18. A method for vaccination against avian influenza infection in a subject in need thereof, comprising:
    administering to the subject in need thereof the adjuvanted influenza vaccine composition of claim 10.

19. The method of claim 18, wherein the subject is at least one selected from the group consisting of humans and birds.

* * * * *

SEQUENCE LISTING

```
<160> NUMBER OF SEQ ID NOS: 8

<210> SEQ ID NO 1
<211> LENGTH: 241
<212> TYPE: PRT
<213> ORGANISM: Foot-and-mouth disease virus

<400> SEQUENCE: 1

Met Ala Ser Met Thr Gly Gly Gln Gln Met Gly Arg Gly Ser Gly Ile
1               5                   10                  15

Phe Pro Val Ala Cys Ser Asp Gly Tyr Gly Gly Leu Val Thr Thr Asp
            20                  25                  30

Pro Lys Thr Ala Asp Pro Val Tyr Gly Lys Val Phe Asn Pro Pro Arg
        35                  40                  45

Asn Leu Leu Pro Gly Arg Phe Thr Asn Leu Leu Asp Val Ala Glu Ala
    50                  55                  60

Cys Pro Thr Phe Leu His Phe Asp Gly Asp Val Pro Tyr Val Thr Thr
```

```
                65                   70                  75                   80
Lys Thr Asp Ser Asp Arg Val Leu Ala Gln Phe Asp Leu Ser Leu Ala
                    85                   90                  95

Ala Lys His Met Ser Asn Thr Phe Leu Ala Gly Leu Ala Gln Tyr Tyr
                    100                 105                  110

Thr Gln Tyr Ser Gly Thr Ile Asn Leu His Phe Met Phe Thr Gly Pro
                    115                 120                  125

Thr Asp Ala Lys Ala Arg Tyr Met Val Ala Tyr Ala Pro Pro Gly Met
                130                  135                 140

Glu Pro Pro Lys Thr Pro Glu Ala Ala Ala His Cys Ile His Ala Glu
145                  150                 155                  160

Trp Asp Thr Gly Leu Asn Ser Lys Phe Thr Phe Ser Ile Pro Tyr Leu
                    165                 170                  175

Ser Ala Ala Asp Tyr Ala Tyr Thr Ala Ser Asp Asx Ala Glu Thr Thr
                180                  185                 190

Met Asx Gln Gly Trp Asx Cys Leu Phe Gln Ile Thr His Gly Lys Ala
                    195                 200                  205

Asp Gly Asp Ala Leu Val Val Leu Ala Ser Ala Gly Lys Asp Phe Asp
                210                  215                 220

Leu Arg Leu Pro Val Asp Ala Arg Thr Gln Leu Glu His His His His
225                  230                 235                  240

His

<210> SEQ ID NO 2
<211> LENGTH: 220
<212> TYPE: PRT
<213> ORGANISM: Foot-and-mouth disease virus

<400> SEQUENCE: 2

Gly Ile Phe Pro Val Ala Cys Ser Asp Gly Tyr Gly Gly Leu Val Thr
1                   5                   10                  15

Thr Asp Pro Lys Thr Ala Asp Pro Val Tyr Gly Lys Val Phe Asn Pro
                    20                  25                  30

Pro Arg Asn Leu Leu Pro Gly Arg Phe Thr Asn Leu Leu Asp Val Ala
                35                  40                  45

Glu Ala Cys Pro Thr Phe Leu His Phe Asp Gly Asp Val Pro Tyr Val
            50                  55                  60

Thr Thr Lys Thr Asp Ser Asp Arg Val Leu Ala Gln Phe Asp Leu Ser
65                  70                  75                  80

Leu Ala Ala Lys His Met Ser Asn Thr Phe Leu Ala Gly Leu Ala Gln
                    85                  90                  95

Tyr Tyr Thr Gln Tyr Ser Gly Thr Ile Asn Leu His Phe Met Phe Thr
                    100                 105                 110

Gly Pro Thr Asp Ala Lys Ala Arg Tyr Met Val Ala Tyr Ala Pro Pro
                115                 120                 125

Gly Met Glu Pro Pro Lys Thr Pro Glu Ala Ala Ala His Cys Ile His
            130                 135                 140

Ala Glu Trp Asp Thr Gly Leu Asn Ser Lys Phe Thr Phe Ser Ile Pro
145                 150                 155                 160

Tyr Leu Ser Ala Ala Asp Tyr Ala Tyr Thr Ala Ser Asp Asx Ala Glu
                    165                 170                 175

Thr Thr Met Asx Gln Gly Trp Asx Cys Leu Phe Gln Ile Thr His Gly
                    180                 185                 190

Lys Ala Asp Gly Asp Ala Leu Val Val Leu Ala Ser Ala Gly Lys Asp
```

```
                195                 200                 205
Phe Asp Leu Arg Leu Pro Val Asp Ala Arg Thr Gln
    210                 215                 220

<210> SEQ ID NO 3
<211> LENGTH: 60
<212> TYPE: PRT
<213> ORGANISM: Foot-and-mouth disease virus

<400> SEQUENCE: 3

Leu Ala Gly Leu Ala Gln Tyr Tyr Thr Gln Tyr Ser Gly Thr Ile Asn
1               5                   10                  15
Leu His Phe Met Phe Thr Gly Pro Thr Asp Ala Lys Ala Arg Tyr Met
            20                  25                  30
Val Ala Tyr Ala Pro Pro Gly Met Glu Pro Pro Lys Thr Pro Glu Ala
        35                  40                  45
Ala Ala His Cys Ile His Ala Glu Trp Asp Thr Gly
    50                  55                  60

<210> SEQ ID NO 4
<211> LENGTH: 330
<212> TYPE: PRT
<213> ORGANISM: Foot-and-mouth disease virus

<400> SEQUENCE: 4

His His His His His Met Ser Asp Ser Glu Val Asn Gln Glu Ala
1               5                   10                  15
Lys Pro Glu Val Lys Pro Glu Val Lys Pro Glu Thr His Ile Asn Leu
            20                  25                  30
Lys Val Ser Asp Gly Ser Ser Glu Ile Phe Phe Lys Ile Lys Lys Thr
        35                  40                  45
Thr Pro Leu Arg Arg Leu Met Glu Ala Phe Ala Lys Arg Gln Gly Lys
    50                  55                  60
Glu Met Asp Ser Leu Arg Phe Leu Tyr Asp Gly Ile Arg Ile Gln Ala
65                  70                  75                  80
Asp Gln Thr Pro Glu Asp Leu Asp Met Glu Asp Asn Asp Ile Ile Glu
                85                  90                  95
Ala His Arg Glu Gln Ile Gly Gly Ala Thr Tyr Gly Gly Met Gly Ile
            100                 105                 110
Phe Pro Val Ala Cys Ser Asp Gly Tyr Gly Gly Leu Val Thr Thr Asp
        115                 120                 125
Pro Lys Thr Ala Asp Pro Val Tyr Gly Lys Val Phe Asn Pro Pro Arg
    130                 135                 140
Asn Leu Leu Pro Gly Arg Phe Thr Asn Leu Leu Asp Val Ala Glu Ala
145                 150                 155                 160
Cys Pro Thr Phe Leu His Phe Asp Gly Asp Val Pro Tyr Val Thr Thr
                165                 170                 175
Lys Thr Asp Ser Asp Arg Val Leu Ala Gln Phe Asp Leu Ser Leu Ala
            180                 185                 190
Ala Lys His Met Ser Asn Thr Phe Leu Ala Gly Leu Ala Gln Tyr Tyr
        195                 200                 205
Thr Gln Tyr Ser Gly Thr Ile Asn Leu His Phe Met Phe Thr Gly Pro
    210                 215                 220
Thr Asp Ala Lys Ala Arg Tyr Met Val Ala Tyr Ala Pro Pro Gly Met
225                 230                 235                 240
Glu Pro Pro Lys Thr Pro Glu Ala Ala Ala His Cys Ile His Ala Glu
```

```
                    245                 250                 255

Trp Asp Thr Gly Leu Asn Ser Lys Phe Thr Phe Ser Ile Pro Tyr Leu
                260                 265                 270

Ser Ala Ala Asp Tyr Ala Tyr Thr Ala Ser Asp Asx Ala Glu Thr Thr
            275                 280                 285

Met Asx Gln Gly Trp Asx Cys Leu Phe Gln Ile Thr His Gly Lys Ala
        290                 295                 300

Asp Gly Asp Ala Leu Val Val Leu Ala Ser Ala Gly Lys Asp Phe Asp
305                 310                 315                 320

Leu Arg Leu Pro Val Asp Ala Arg Thr Gln
                325                 330

<210> SEQ ID NO 5
<211> LENGTH: 252
<212> TYPE: PRT
<213> ORGANISM: Avian influenza virus

<400> SEQUENCE: 5

Met Ser Leu Leu Thr Glu Val Glu Thr Tyr Val Leu Ser Ile Val Pro
1               5                   10                  15

Ser Gly Pro Leu Lys Ala Glu Ile Ala Gln Arg Leu Glu Asp Val Phe
            20                  25                  30

Ala Gly Lys Asn Thr Asp Leu Glu Ala Leu Met Glu Trp Leu Lys Thr
        35                  40                  45

Arg Pro Ile Leu Ser Pro Leu Thr Lys Gly Ile Leu Gly Phe Val Phe
    50                  55                  60

Thr Leu Thr Val Pro Ser Glu Arg Gly Leu Gln Arg Arg Arg Phe Val
65                  70                  75                  80

Gln Asn Ala Leu Asn Gly Asn Gly Asp Pro Asn Asn Met Asp Lys Ala
                85                  90                  95

Val Lys Leu Tyr Arg Lys Leu Lys Arg Glu Ile Thr Phe His Gly Ala
            100                 105                 110

Lys Glu Ile Ala Leu Ser Tyr Ser Ala Gly Ala Leu Ala Ser Cys Met
        115                 120                 125

Gly Leu Ile Tyr Asn Arg Met Gly Ala Val Thr Thr Glu Val Ala Phe
    130                 135                 140

Gly Leu Val Cys Ala Thr Cys Glu Gln Ile Ala Asp Ser Gln His Arg
145                 150                 155                 160

Ser His Arg Gln Met Val Ala Thr Thr Asn Pro Leu Ile Arg His Glu
                165                 170                 175

Asn Arg Met Val Leu Ala Ser Thr Thr Ala Lys Ala Met Glu Gln Met
            180                 185                 190

Ala Gly Ser Ser Glu Gln Ala Ala Glu Ala Met Glu Ile Ala Ser Gln
        195                 200                 205

Ala Arg Gln Met Val Gln Ala Met Arg Ala Ile Gly Thr His Pro Ser
    210                 215                 220

Ser Ser Thr Gly Leu Arg Asp Asp Leu Leu Glu Asn Leu Gln Thr Tyr
225                 230                 235                 240

Gln Lys Arg Met Gly Val Gln Met Gln Arg Phe Lys
                245                 250

<210> SEQ ID NO 6
<211> LENGTH: 97
<212> TYPE: PRT
<213> ORGANISM: Avian influenza virus
```

<400> SEQUENCE: 6

```
Met Ser Leu Leu Thr Glu Val Glu Thr Pro Ile Arg Asn Glu Trp Gly
1               5                   10                  15
Cys Arg Cys Asn Asp Ser Ser Asp Pro Leu Val Val Ala Ala Asn Ile
                20                  25                  30
Ile Gly Ile Leu His Leu Ile Leu Trp Ile Leu Asp Arg Leu Phe Phe
            35                  40                  45
Lys Cys Val Tyr Arg Leu Phe Lys His Gly Leu Lys Arg Gly Pro Ser
        50                  55                  60
Thr Glu Gly Val Pro Glu Ser Met Arg Glu Tyr Arg Lys Glu Gln
65                  70                  75                  80
Gln Asn Ala Val Asp Ala Asp Ser His Phe Val Ser Ile Glu Leu
                85                  90                  95
Glu
```

<210> SEQ ID NO 7
<211> LENGTH: 564
<212> TYPE: PRT
<213> ORGANISM: Avian influenza virus

<400> SEQUENCE: 7

```
Met Glu Arg Ile Val Ile Ala Phe Ala Ile Val Asn Ile Val Thr Gly
1               5                   10                  15
Asp Arg Ile Cys Ile Gly Tyr His Ala Asn Asn Ser Thr Thr Gln Val
                20                  25                  30
Asp Thr Ile Met Glu Lys Asn Val Thr Val Thr His Ala Gln Asp Ile
            35                  40                  45
Leu Glu Lys Glu His Asn Gly Arg Leu Cys Ser Leu Lys Gly Val Lys
        50                  55                  60
Pro Leu Ile Leu Lys Asn Cys Ser Val Ala Gly Trp Leu Leu Gly Asn
65                  70                  75                  80
Pro Met Cys Asp Glu Phe Leu Asn Ala Pro Glu Trp Ser Tyr Ile Val
                85                  90                  95
Glu Lys Asp Arg Pro Ser Asn Gly Leu Cys Tyr Pro Gly Thr Phe Asn
            100                 105                 110
Tyr Tyr Glu Glu Leu Lys His Leu Met Ser Ser Thr Asn Gln Phe Glu
        115                 120                 125
Lys Ile Gln Ile Phe Pro Arg Ser Ser Trp Ser Asn His Asp Ala Ser
    130                 135                 140
Ser Gly Val Ser Ser Ala Cys Pro Tyr Asn Gly Arg Ser Ser Phe Phe
145                 150                 155                 160
Arg Asn Val Val Trp Leu Ile Lys Lys Asn Asn Val Tyr Arg Thr Ile
                165                 170                 175
Thr Arg Thr Tyr Asn Asn Thr Asn Ile Glu Asp Leu Leu Ile Ile Trp
            180                 185                 190
Gly Ile His His Pro Asn Asn Ala Ala Glu Gln Ile Lys Leu Tyr Gln
        195                 200                 205
Asn Pro Ser Thr Tyr Val Ser Val Gly Thr Ser Thr Leu Asn Gln Arg
    210                 215                 220
Ser Ile Pro Glu Ile Ala Thr Arg Pro Lys Val Asn Gly Gln Ser Gly
225                 230                 235                 240
Arg Met Glu Phe Phe Trp Thr Ile Leu Arg Pro Asn Asp Ser Ile Thr
                245                 250                 255
Phe Glu Ser Thr Gly Asn Phe Ile Ala Pro Glu Tyr Ala Tyr Lys Ile
```

-continued

```
                260                 265                 270
        Val Lys Lys Gly Asp Ser Ala Ile Met Lys Ser Glu Leu Ser Tyr Ser
                    275                 280                 285

Asn Cys Asp Thr Lys Cys Gln Thr Pro Val Gly Ala Ile Asn Ser Ser
                    290                 295                 300

Met Pro Phe His Asn Val His Pro Phe Ala Ile Gly Glu Cys Pro Lys
        305                 310                 315                 320

Tyr Val Lys Leu Lys Lys Leu Val Leu Ala Thr Gly Leu Arg Asn Ile
                        325                 330                 335

Pro Gln Arg Arg Lys Arg Gly Leu Phe Gly Ala Ile Ala Gly Phe Ile
                    340                 345                 350

Glu Gly Gly Trp Gln Gly Met Val Asp Gly Trp Tyr Gly Tyr His His
                    355                 360                 365

Ser Asn Glu Gln Gly Ser Gly Tyr Ala Ala Asp Lys Glu Ser Thr Gln
                    370                 375                 380

Lys Ala Val Asp Gly Ile Thr Asn Lys Val Asn Ser Ile Ile Ser Lys
        385                 390                 395                 400

Met Asn Ser Gln Phe Glu Ala Val Gly Lys Glu Phe Asn Asn Leu Glu
                        405                 410                 415

Arg Arg Ile Glu Asn Leu Asn Lys Lys Met Glu Asp Gly Phe Ile Asp
                    420                 425                 430

Val Trp Thr Tyr Asn Ala Glu Leu Leu Val Leu Met Glu Asn Glu Arg
                    435                 440                 445

Thr Leu Asp Leu His Asp Ser Asn Val Lys Asn Leu Tyr Asp Lys Val
        450                 455                 460

Arg Arg Gln Leu Arg Asp Asn Ala Lys Glu Leu Gly Asn Gly Cys Phe
        465                 470                 475                 480

Glu Phe Tyr His Arg Cys Asp Asn Lys Cys Met Glu Ser Val Arg Asn
                        485                 490                 495

Gly Thr Tyr Asp Tyr Pro Gln Tyr Ser Glu Glu Ser Arg Leu Lys Arg
                    500                 505                 510

Glu Glu Ile Asp Gly Val Lys Leu Glu Ser Met Gly Val Tyr Gln Ile
                    515                 520                 525

Ile Ser Ile Tyr Ser Thr Val Ala Ser Ser Leu Ala Leu Ala Ile Met
                530                 535                 540

Val Ala Gly Leu Ser Phe Trp Met Cys Ser Asn Gly Ser Leu Gln Cys
        545                 550                 555                 560

Arg Val Cys Ile

<210> SEQ ID NO 8
<211> LENGTH: 449
<212> TYPE: PRT
<213> ORGANISM: Avian influenza virus

<400> SEQUENCE: 8

Met Asn Pro Asn Gln Lys Ile Ile Thr Ile Gly Ser Val Ser Leu Thr
        1               5                   10                  15

Ile Ala Thr Val Cys Phe Leu Met Gln Ile Ala Ile Leu Thr Met Thr
                        20                  25                  30

Val Thr Leu His Phe Asn Gln Asn Glu Cys Ser Ile Pro Ala Asn Asn
                    35                  40                  45

Gln Val Val Pro Cys Glu Pro Ile Ile Ile Glu Lys Ser Ile Asn Tyr
                50                  55                  60

Arg Asp Trp Ser Lys Pro Gln Cys Arg Ile Thr Gly Phe Ala Pro Phe
```

```
                65                  70                  75                  80
       Ser Lys Asp Asn Ser Ile Arg Leu Ser Ala Gly Gly Asn Ile Trp Val
                        85                  90                  95

Thr Arg Glu Pro Tyr Val Ser Cys Asp Thr Ser Lys Cys Tyr Gln Phe
                       100                 105                 110

Ala Leu Gly Gln Gly Thr Thr Leu Asp Asn Lys His Ser Asn Gly Thr
                       115                 120                 125

Ile His Asp Arg Thr Pro His Arg Thr Leu Leu Met Ser Glu Leu Gly
                       130                 135                 140

Val Pro Phe His Leu Gly Thr Lys Gln Val Cys Ile Ala Trp Ser Ser
       145                 150                 155                 160

Ser Ser Cys His Asp Gly Lys Ala Trp Leu His Val Cys Val Thr Gly
                       165                 170                 175

Asp Asp Lys Asn Ala Thr Ala Ser Phe Ile Tyr Asp Gly Met Leu Val
                       180                 185                 190

Asp Ser Ile Gly Ser Trp Ser Gln Asn Ile Leu Arg Thr Gln Glu Ser
                       195                 200                 205

Glu Cys Val Cys Ile Asn Gly Thr Cys Thr Val Val Met Thr Asp Gly
                       210                 215                 220

Ser Ala Ser Gly Lys Ala Asp Thr Arg Ile Leu Phe Ile Glu Glu Gly
       225                 230                 235                 240

Gln Val Ile His Ile Ser Pro Leu Ser Gly Ser Ala Gln His Ile Glu
                       245                 250                 255

Glu Cys Ser Cys Tyr Pro Arg Tyr Pro Asn Val Arg Cys Val Cys Arg
                       260                 265                 270

Asp Asn Trp Lys Gly Ser Asn Arg Pro Val Val Asp Ile Asn Met Ala
                       275                 280                 285

Asp Tyr Ser Ile Asp Ser Ser Tyr Val Cys Ser Gly Leu Val Gly Asp
                       290                 295                 300

Thr Pro Arg Asn Asp Asp Ser Ser Ser Ser Asn Cys Arg Asp Pro
       305                 310                 315                 320

Asn Asn Glu Lys Gly Asn Pro Gly Val Lys Gly Trp Ala Phe Asp Asp
                       325                 330                 335

Gly Asp Asp Ile Trp Met Gly Arg Thr Ile Ser Lys Asp Ser Arg Ser
                       340                 345                 350

Gly Tyr Glu Thr Phe Arg Val Ile Asp Gly Trp Thr Ile Ala Asn Ser
                       355                 360                 365

Lys Ser Gln Ile Asn Arg Gln Val Ile Val Asp Asn Asn Trp Ser
                       370                 375                 380

Gly Tyr Ser Gly Ile Phe Ser Val Glu Asn Lys Ser Cys Ile Asn Arg
       385                 390                 395                 400

Cys Phe Tyr Val Glu Leu Ile Arg Gly Arg Pro Lys Glu Thr Arg Val
                       405                 410                 415

Trp Trp Thr Ser Asn Ser Ile Val Ala Phe Cys Gly Thr Ser Gly Thr
                       420                 425                 430

Tyr Gly Thr Gly Ser Trp Pro Asp Gly Ala Asn Ile Asn Phe Met Pro
                       435                 440                 445

Ile
```

UNITED STATES PATENT AND TRADEMARK OFFICE
CERTIFICATE OF CORRECTION

PATENT NO. : 10,391,163 B2
APPLICATION NO. : 15/756774
DATED : August 27, 2019
INVENTOR(S) : Shu-Mei Liang et al.

It is certified that error appears in the above-identified patent and that said Letters Patent is hereby corrected as shown below:

In the Claims

Column 22, Line 29, delete "4" and substitute -- 7 --

Column 22, Line 31, delete "4" and substitute -- 16 --

Signed and Sealed this
Twenty-fourth Day of December, 2019

Andrei Iancu
*Director of the United States Patent and Trademark Office*